(12) United States Patent
Takahashi

(10) Patent No.: US 9,427,140 B2
(45) Date of Patent: Aug. 30, 2016

(54) OPTICAL SYSTEM

(75) Inventor: Susumu Takahashi, Iruma (JP)

(73) Assignee: Olympus Corporation, Tokyo (JP)

( * ) Notice: Subject to any disclaimer, the term of this patent is extended or adjusted under 35 U.S.C. 154(b) by 874 days.

(21) Appl. No.: 12/653,927

(22) Filed: Dec. 17, 2009

(65) Prior Publication Data

US 2010/0195007 A1 Aug. 5, 2010

(51) Int. Cl.
*A61B 1/04* (2006.01)
*A61B 1/00* (2006.01)
*G02B 13/06* (2006.01)
*G02B 23/24* (2006.01)

(52) U.S. Cl.
CPC .............. *A61B 1/04* (2013.01); *A61B 1/00096* (2013.01); *A61B 1/00177* (2013.01); *A61B 1/00179* (2013.01); *A61B 1/00181* (2013.01); *G02B 13/06* (2013.01); *G02B 23/243* (2013.01)

(58) Field of Classification Search
CPC  G02B 23/243; G02B 23/2438; G02B 13/06; A61B 1/00096; A61B 1/00177; A61B 1/00179; A61B 1/00181; A61B 1/04
USPC ............................................ 348/67; 359/367
See application file for complete search history.

(56) References Cited

U.S. PATENT DOCUMENTS

| 4,843,242 A | * | 6/1989 | Doyle | 250/330 |
| 4,902,115 A | * | 2/1990 | Takahashi | 359/362 |
| 2004/0249247 A1 | * | 12/2004 | Iddan | 600/170 |

FOREIGN PATENT DOCUMENTS

| JP | 09-248276 | | 9/1997 | |
| JP | 11-137512 | | 5/1999 | |
| JP | 2002-523801 | | 7/2002 | |
| JP | 2002-341409 | | 11/2002 | |
| JP | 2004-312593 | | 11/2004 | |
| JP | 2005-261557 | | 9/2005 | |
| JP | 2005261557 A | * | 9/2005 | ............... A61B 1/00 |

* cited by examiner

*Primary Examiner* — Jessica M Merlin
(74) *Attorney, Agent, or Firm* — Kenyon & Kenyon LLP

(57) ABSTRACT

The present optical system comprises a forward observation optical system, an entire lateral circumference-observation optical system, a variable stop arranged on the image side of the observation optical system, an image-forming optical system, and an image pickup element, and the variable stop is formed so as to be capable of switching an observation field of view at least to a first observation field of view including only a forward field of view and to a second observation field of view including a forward field of view with a narrower angle than that of the first observation field of view and a field of view of the entire lateral circumference. The observation optical system is arranged on the object side of the opening in the central position of the observation optical system. The variable stop intercepts an optical path for the observation optical system when an observation field of view is switched to the first observation field of view, and opens the optical path for the observation optical system when an observation field of view is switched to the second observation field of view.

2 Claims, 12 Drawing Sheets

OPTICAL SYSTEM

This application claims benefits of Japanese Patent Application No. 2008-292416 filed in Japan on Nov. 14, 2008, the contents of which are hereby incorporated by reference.

BACKGROUND OF THE INVENTION

1. Field of the Invention

This invention relates to an optical system provided with a forward observation optical system and an entire lateral circumference-observation optical system.

2. Description of the Related Art

Optical systems which are disclosed, for example, in Japanese Patent Kokai No. 2005-261557, Japanese Patent Kokai No. Hei 9-248276, and Japanese Patent Kokai No. Hei 11-137512 respectively have been conventionally proposed as this kind of optical system. These optical systems are formed in such a way that it is possible to switch to various observation fields of view.

The optical system disclosed in Japanese Patent Kokai No. 2005-261557 is used for an endoscope in which the direction of a field of view can be changed. As shown in FIG. 1A, a direct-looking observation optical system 52 for an observation in the direction along an axis O1 of an insertion section 51, and a side-looking observation optical system 53 for an observation in the direction perpendicular to the axis O1 of the insertion section 51 are arranged in the tip portion of the insertion section 51. In FIG. 1A, 52a denotes an objective optical system for the direct-looking observation optical system 52, 53a denotes an objective optical system for the side-looking observation optical system 53, and 53b denotes a mirror which deflects light from the objective optical system 52a in the direction parallel to the optical axis of the direct-looking observation optical system 52. Also, an image-forming optical system 54 and a CCD 55 are arranged on the optical path common to the direct-looking observation optical system 52 and the side-looking observation optical system 53. Further, a rotary shutter 56 is arranged between: the objective optical system 52a and the mirror 53b; and the image-forming optical system 54. As shown in FIG. 1B, a through hole 57 as a stop is provided for the rotary shutter 56.

And, the optical system is formed in such a way that it is possible to acquire either: a three-dimensional observation image of an portion P in front of the insertion section 51 in the direction along the axis O1; or observation images of an portion Pin front of the insertion section 51 in the direction along the axis O1 and of an portion P' in the direction different from the direction of the portion P in front of the insertion section in the direction along the axis O1, by rotating the rotary shutter 56 arranged on the optical axes of the objective optical systems 52a and 53a to selectively form an image by light flux passing through the through hole 57 by the CCD 55.

Also, the optical system disclosed in Japanese Patent Kokai No. Hei 9-248276 is used for a rigid endoscope in which the direction of a field of view can be changed. As shown in FIG. 2A, the optical system is provided with: an objective optical system 61, a relay lens system 62, and an eyepiece optical system 63 on the rigid-endoscope-60 side; and an image-forming optical system 65 and an image pickup element 66 on the TV-camera-64 side. The objective optical system 61 is provided with a front lens group 61' which consists of: two objective lenses 61a and 61b which are arranged at the nearest position to an object and face toward the direct-looking direction and toward the side-looking direction respectively; a first prism 61c which light beams from the two objective lenses enter through its planes which differ from each other, respectively; a second prism 61d which light beams from the first prism 61c enter through the identical plane of the second prism; and a pupil-separating stop 61e which makes a separation of pupils 61ea and 61eb according to the above-described directions of fields of view (the direct-looking and side-looking directions). A rear lens group 61" is arranged in the rear of the front lens group 61' and the rear lens group 61" is used for focusing light beams from the pupils 61ea and 61eb to form the image of an object.

An image $I_1$ from more than one direction of a field of view which is formed through the objective optical system 61, and the pupils 61ea and 61eb are propagated toward the eyepiece optical system 63 by the relay lens system 62. In FIG. 2B, $P_2$ denotes more than one pupil which is propagated by the relay lens system 62 and corresponds to the direction of each of the fields of view. An image $I_2$ is formed between the relay lens system 62 and the eyepiece optical system 63, and more than one pupil $P_3$ which corresponds to the direction of each of the fields of view is acquired through the eyepiece optical system 63.

A pupil-selecting stop 67 as a means for selecting the direction of a field of view is arranged in the rear of the pupils $P_3$. The pupil-selecting stop 67 is provided with an opening section 67a which transmits light of only either the pupil 61ea or 61eb. And, the pupil-selecting stop 67 is arranged with the direction of the opening section 67a optionally selected, and it is possible to acquire an observation image in the direction of a field of view of either the direct-looking or side-looking direction, by imaging a light beam transmitted by the opening section 67a by the image pickup element 66.

Also, the optical system disclosed in Japanese Patent Kokai No. Hei 11-137512 is used for an endoscope in which the direction of a field of view can be changed. As shown in FIGS. 3A and 3B, a tip rigid section 71 is provided with a direct-looking objective lens 72, a side-looking objective lens 73, a mirror 74, and a solid-state image pickup device 75. The mirror 74 is formed so as to be capable of rotating on a driving element 76 through the driving element 76. In FIG. 3B, 77 denotes a light-intercepting plate which shields from light the surface of the mirror 74 on the direct-looking-objective-lens-72 side.

And, by the mirror 74 rotated by the driving element 76 and switching to light from the direct-looking objective lens 72 or to light from the side-looking objective lens 73 to make the light enter the solid-state image pickup element 75, it is possible to acquire an observation image in the direction of a field of view of either direct-looking or side-looking direction.

Now, in an observation of the inside of a pipe-shaped object using an endoscope or the like, when an observation in the forward field of view is performed in insertion of an endoscope or the like into the inside of the pipe-shaped object and a portion which requires a detailed observation is found in the inner surface of the pipe-shaped object after the insertion, there is a necessity to a detailed observation over the entire circumference of the inner surface of the pipe-shaped object including the portion with respect to the lateral field of view.

Also, for example, in an examination of a stomach, an engine pipe, or the like, an optical system by which it is possible to simultaneously perform observations in the forward field of view and in the field of view of the entire lateral circumference is highly demanded because: in an observation of the side of a pipe, there is fear of mistaking an examination position if it is impossible to identify a position in the direction of the depth of the pipe; and, also, in an endoscope provided with an optical system by which it is possible to perform an observation only in either of the forward field of view or the field of view of the entire lateral circumference, as often as an observation is performed in a different field of view, the endoscope provided with the optical system by which it is possible to perform an observation in a desired observation field of view must be inserted into the inside of the pipe all over again, a physical burden to a subject becomes large, and the work by an examiner becomes complicated.

Also, conventional optical systems by which it is possible to perform a simultaneous observation in the forward field of view and in the field of view of the entire lateral circumference include, for example, optical systems which are disclosed in Japanese Patent Kokai No. 2002-341409, Japanese Patent Kouhyou No. 2002-523801, and Japanese Patent Kokai No. 2004-312593 respectively.

As shown in FIG. 4, the optical system disclosed in Japanese Patent Kokai No. 2002-341409 is provided with a rotationally symmetric convex mirror 81, a camera 82 arranged at a position at which the camera faces the convex mirror 81, a transparent tubular body 83 which joins the convex mirror 81 to the camera 82, and lenses 85 which are placed inside a through hole 84 formed in the central portion of the convex mirror 81 or are placed on the axial line of the through hole 84. In FIG. 4, 82a denotes an image-forming lens and 82b denotes an image pickup element. And, light from the forward field of view passes through the lenses 85 and passes through the image-forming lens 82a to form an image on the central region 86 of the imaging plane of the image pickup element 82b, while light from the field of view of the entire lateral circumference is reflected by the convex lens 81 and passes through the image-forming lens 82a to form an image on the surrounding region 87 of the imaging plane of the image pickup element 82c. By the light forming an image in the above-described manner, it is possible to simultaneously acquire observation images in the forward field of view and in the field of view of the entire lateral circumference.

As shown in FIG. 5, the optical system disclosed in Japanese Patent Kouhyou No. 2002-523801 is provided with: a rotationally symmetric lens block 91 which is provided with convex reflexive surfaces 91a which are formed so as to transmit light from the forward field of view and so as to reflect light from the field of view of the entire lateral circumference; a lens block 92; a lens system 93 which is arranged in the front of the lens block 91; a lens system 94 which is arranged in the rear of the lens block 92; and an image-capturing device 95. And, light from the forward field of view passes through the lens system 93, enters the inside of the lens block 91, and passes through the lens block 93 and the lens system 94 to form an image on the central region of the imaging plane of the image-capturing device 95, while light from the field of view of the entire lateral circumference is reflected by the convex reflexive surfaces 91a and passes through the lens blocks 91, 92, and the lens system 94 to form an image on the surrounding region of the imaging plane of the image-capturing device 95. By the light forming an image in the above-described manner, it is possible to simultaneously acquire observation images in the forward field of view and in the field of view of the entire lateral circumference.

As shown in FIG. 6, the optical system disclosed in Japanese Patent Kokai No. 2004-312593 is provided with: a rotationally-symmetric convex reflexive mirror 101 which is provided with an opening section 101a in its central portion; a rotationally-symmetric reflexive mirror 102 which is arranged so as to face the convex reflexive mirror 101 and is provided with an opening section 102a in its central portion; a lens 103 which is placed in the opening section 102a of the reflexive mirror 102; and an image pickup means 104 which performs imaging by receiving reflexive light which is reflected by the convex reflexive mirror 101 toward the reflexive mirror 102 and is thereafter reflected by the reflexive mirror 102 toward the opening section 101a of the convex reflexive mirror 101 and incident light which is transmitted by the lens 103 and goes in toward the opening section 101a of the convex reflexive mirror 101. Besides, in FIG. 6, 105 denotes a transparent cover and 106 denotes an image-displaying apparatus. And, light from the forward field of view is transmitted by the lens 103 and passes through the opening section 101a to form an image on the central region of the image pickup plane of the image pickup means 104, while light from the field of view of the entire lateral circumference is reflected by the reflexive mirror 102 toward the opening section 101a of the convex reflexive mirror 101 and passes through the opening section 101a to form an image on the central region of the image pickup plane of the image pickup means 104 after the light from the field of view of the entire lateral circumference is transmitted by the transparent cover 105 and is reflected by the convex reflexive mirror 101 toward the reflexive mirror 102. By the light forming an image in the above-described manner, it is possible to simultaneously acquire observation images in the forward field of view and in the field of view of the entire lateral circumference.

As described above, the optical systems which are disclosed in Japanese Patent Kokai No. 2002-341409, Japanese Patent Kouhyou No. 2002-523801, and Japanese Patent Kokai No. 2004-312593 respectively are provided with an optical system which guides light from the forward field of view to an image pickup means, and an optical system which guides light from the field of view of the entire lateral circumference to the image pickup means, and it is possible to simultaneously acquire observation images in the forward field of view and in the field of view of the entire lateral circumference.

Now, in the case of an observation in each of the forward field of view and the field of view of the entire lateral circumference, a small proportion of the image-forming region for an observation image in each of the fields of view in the image pickup region of the image pickup means makes it difficult to perform a detailed observation, so that it is desirable to make a proportion of the image-forming region for an observation image in each of the fields of view in the image pickup region of the image pickup means as large as possible.

Accordingly, in a detailed observation in the field of view of the entire lateral circumference, it is desirable: to make a proportion of the image-forming region for observation images in the forward field of view in the imaging region of the imaging means to such a degree that a position in the direction of the depth of a pipe can be identified; and to make the image-forming region for observation images in the field of view of the entire lateral circumference as large as possible. Also, on the other hand, in a detailed observation in the forward field of view, it is necessary that the image-forming region for an observation image in the forward field of view accounts for the whole image pickup region of the image pickup means.

SUMMARY OF THE INVENTION

An optical system according to the present invention is characterized in that: the optical system comprises a forward observation optical system, an entire lateral circumference-observation optical system, a variable stop which is arranged on the image side of the entire lateral circumference-observation optical system, an image-forming optical system, and an image pickup element; and the variable stop is formed so as to be capable of switching an observation field of view at least to a first observation field of view including only a forward field of view and to a second observation field of view including a forward field of view with a narrower angle than that of the first observation field of view and a field of view of the entire lateral circumference.

Also, in an optical system of the present invention, it is preferred that the entire lateral circumference-observation optical system is provided with an opening in its central portion, and the forward observation optical system is arranged on the object side of the opening.

Also, in an optical system of the present invention, it is preferred that the variable stop is formed so as to intercept an optical path for the entire lateral circumference-observation optical system when an observation field of view is switched to the first observation field of view.

Also, in an optical system of the present invention, it is preferred that the variable stop is formed so as to open an optical path for the entire lateral circumference-observation optical system when an observation field of view is switched to the second observation field of view.

Also, in an optical system of the present invention, it is preferred that the variable stop comprises two stops which are arranged between the entire lateral circumference-observation optical system and the image-forming optical system and the two stops are formed in such a way that, when one of the two stops is opened, the other stop is stopped down.

Also, in an optical system of the present invention, it is preferred that the variable stop moves on the optical axis between the entire lateral circumference-observation optical system and the image-forming optical system.

Also, in an optical system of the present invention, it is preferred that the image-forming optical system and the image pickup element move integratedly with the variable stop.

Also, in an optical system of the present invention, it is preferred that the variable stop is formed so as to be further also capable of switching an observation field of view to a third observation field of view which includes only a field of view of the entire lateral circumference.

Also, in an optical system of the present invention, it is preferred that the variable stop is formed so as to open an optical path for the entire lateral circumference-observation optical system while the variable stop intercepts an optical path for the forward observation optical system when an observation field of view is switched to the third observation field of view.

Also, in an optical system of the present invention, it is preferred that the variable stop comprises a liquid crystal element.

Also, in an optical system of the present invention, it is preferred that the variable stop is formed in such a way that: the variable stop comprises two liquid crystal elements which are arranged between the entire lateral circumference-observation optical system and the image-forming optical system; when an observation field of view is switched to the first observation field of view, one of the two liquid crystal elements intercepts an optical path for the entire lateral circumference-observation optical system while the other liquid crystal element opens an optical path; when an observation field of view is switched to the second observation field of view, the one liquid crystal element opens an optical path for the entire lateral circumference-observation optical system while the other liquid crystal element stops down an optical path; and, when an observation field of view is switched to the third observation field of view, the one liquid crystal element opens an optical path for the entire lateral circumference-observation optical system and intercepts an optical path for the forward observation optical system while the other liquid crystal element stops down an optical path.

According to the present invention, it is possible to acquire an optical system in which: an observation can be switched to an observation only in a forward field of view and to a simultaneous observation in a forward field of view and in a field of view of the entire lateral circumference; and it is possible to observe an observation image in the field of view of the entire lateral circumference in detail in the observation state in an simultaneous observation in a forward field of view and in the field of view of the entire lateral circumference.

These and other features and advantages of the present invention will become apparent from the following detailed description of the preferred embodiments when taken in conjunction with the accompanying drawings.

DETAILED DESCRIPTION OF THE PREFERRED EMBODIMENTS

Embodiment 1

Figure 7A:
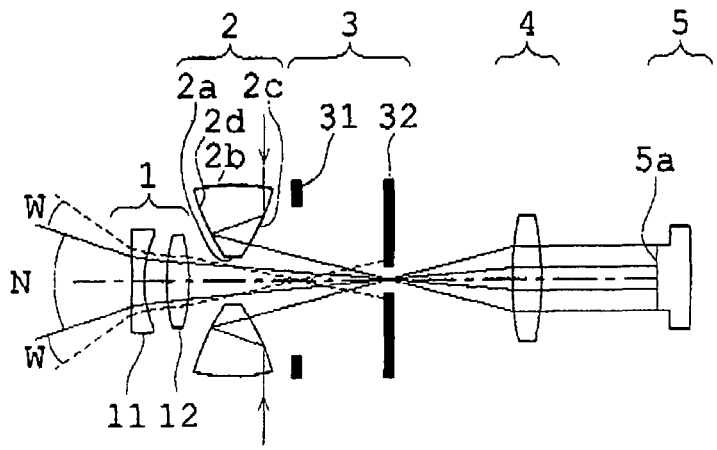
FIGS. 7A, 7B, 7C, and 7D are illustrations showing the schematic formation of an optical system according to the first embodiment of the present invention, and show: a sectional view taken along the optical axis and showing an observation state in a simultaneous observation in a forward field of view and in a field of view of the entire lateral circumference; an illustration showing an image-forming region for an observation image in each of the forward field of view and the field of view of the entire lateral circumference in the imaging plane of an image pickup element in the observation state shown in FIG. 7A; a sectional view taken along the optical axis and showing an observation state in an observation only in a forward field of view; and an illustration showing an image-forming region for an observation image in the field of view of the entire lateral circumference in the imaging plane of the image pickup element in the observation state shown in FIG. 7C, respectively.
Figure 7B:
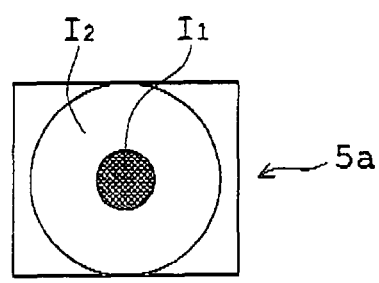
Figure 7C:
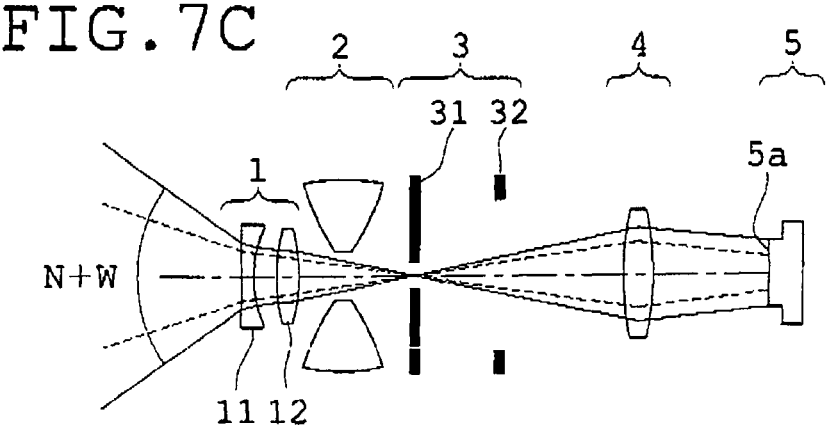
Figure 7D:
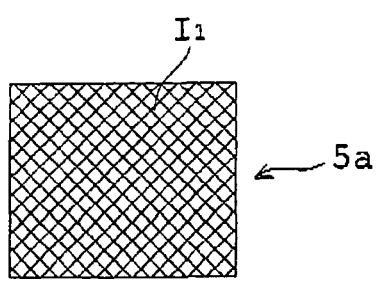
Figure 8A:
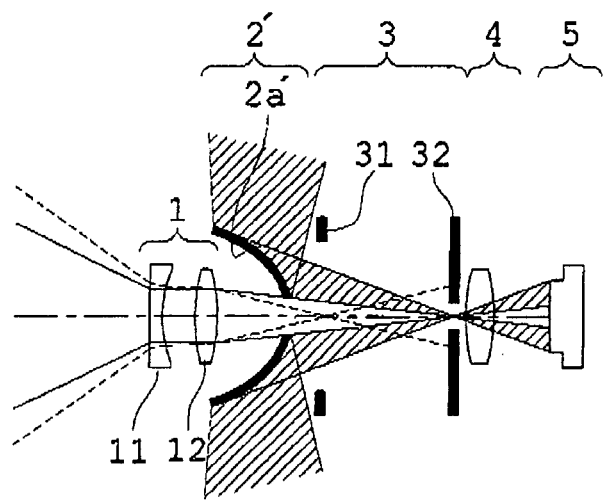
FIGS. 8A and 8B are illustrations showing one example of variations of the optical system shown in FIG. 7, and show: a sectional view taken along the optical axis and showing an observation state in a simultaneous observation in a forward field of view and in the field of view of the entire lateral circumference; and a sectional view taken along the optical axis and showing an observation state in a observation only in a forward field of view, respectively.
Figure 8B:
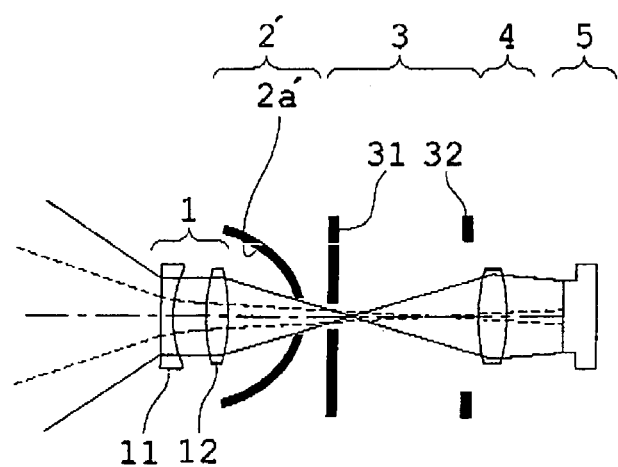

FIGS. 7A, 7B, 7C, and 7D are illustrations showing the schematic formation of an optical system according to the first embodiment of the present invention, and FIG. 7A is a sectional view taken along the optical axis and showing an observation state in a simultaneous observation in a forward field of view and in a field of view of the entire lateral circumference, FIG. 7B is an illustration showing an image-forming region for an observation image in each of the forward field of view and the field of view of the entire lateral circumference in the image pickup plane of an image pickup element in the observation state shown in FIG. 7A, FIG. 7C is a sectional view taken along the optical axis and showing an observation state in an observation only in a forward field of view, and FIG. 7D is an illustration showing an image-forming region for an observation image in the field of view of the entire lateral circumference in the image pickup plane of the image pickup element in the observation state shown in FIG. 7C. FIGS. 8A and 8B are illustrations showing one example of variations of the optical system shown in FIG. 7, and FIG. 8A is a sectional view taken along the optical axis and showing an observation state in a simultaneous observation in a forward field of view and in a field of view of the entire lateral circumference, and FIG. 8B is a sectional view taken along the optical axis and showing an observation state in a observation only in a forward field of view.

The optical system of the first embodiment comprises a forward observation optical system 1, an entire lateral circumference-observation optical system 2, a variable stop 3, an image-forming optical system 4, and an image pickup element 5.

The forward observation optical system 1 is an optical system for performing an observation in a forward field of view, is arranged on the object side of the entire lateral circumference-observation optical system 2, and is composed of a concave lens 11 and a convex lens 12. Besides, lens components which constitute the forward observation optical system 1 are not limited to the formation shown in FIG. 7.

Figure 1A:
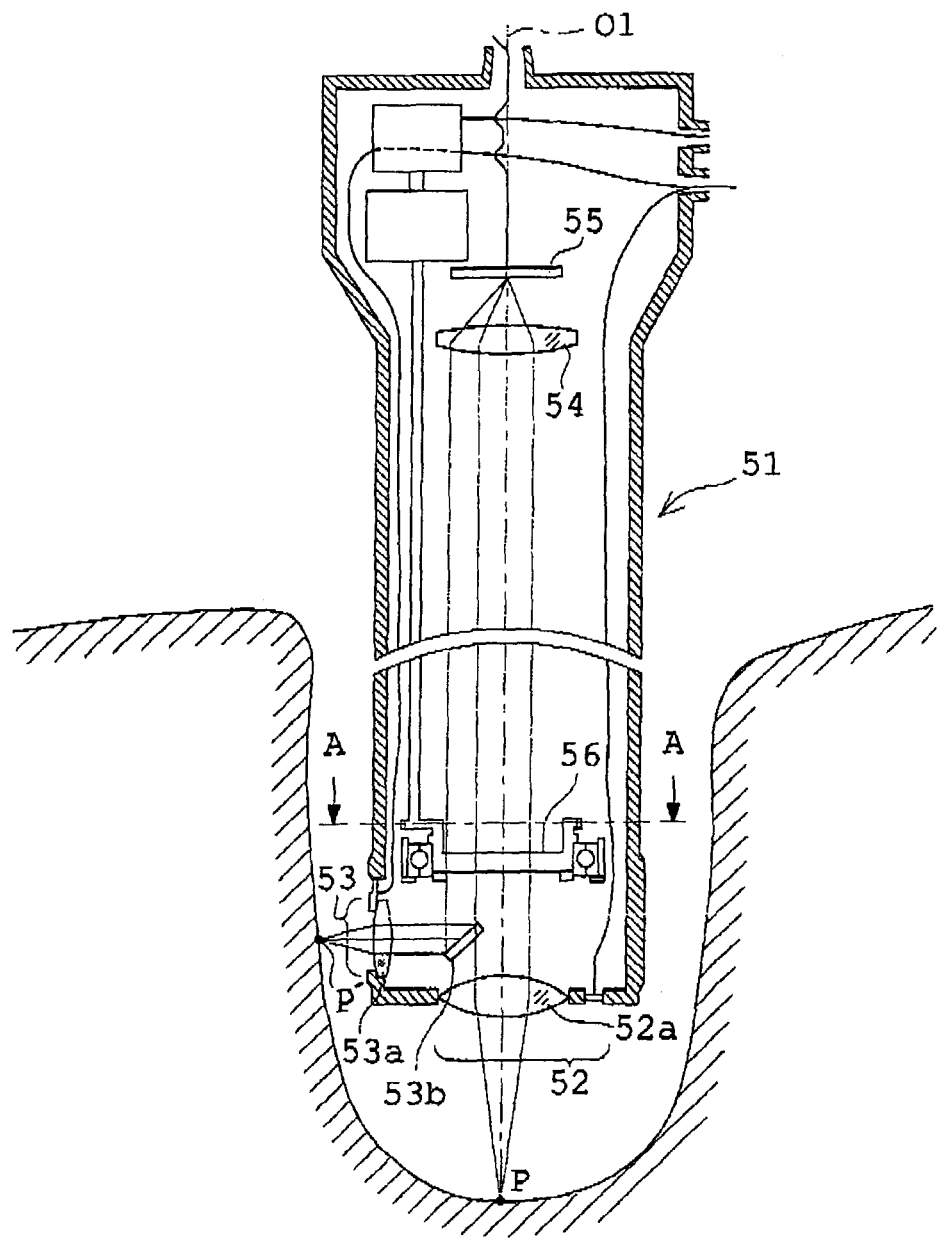
FIGS. 1A and 1B are illustrations showing one conventional example of an optical system which is capable of switching an observation field of view, and show a sectional view along the optical axis and an A-A sectional view of FIG. 1A, respectively.
Figure 1B:
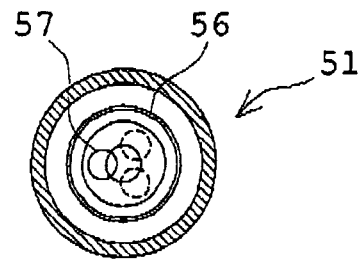
Figures 2A, 2B:
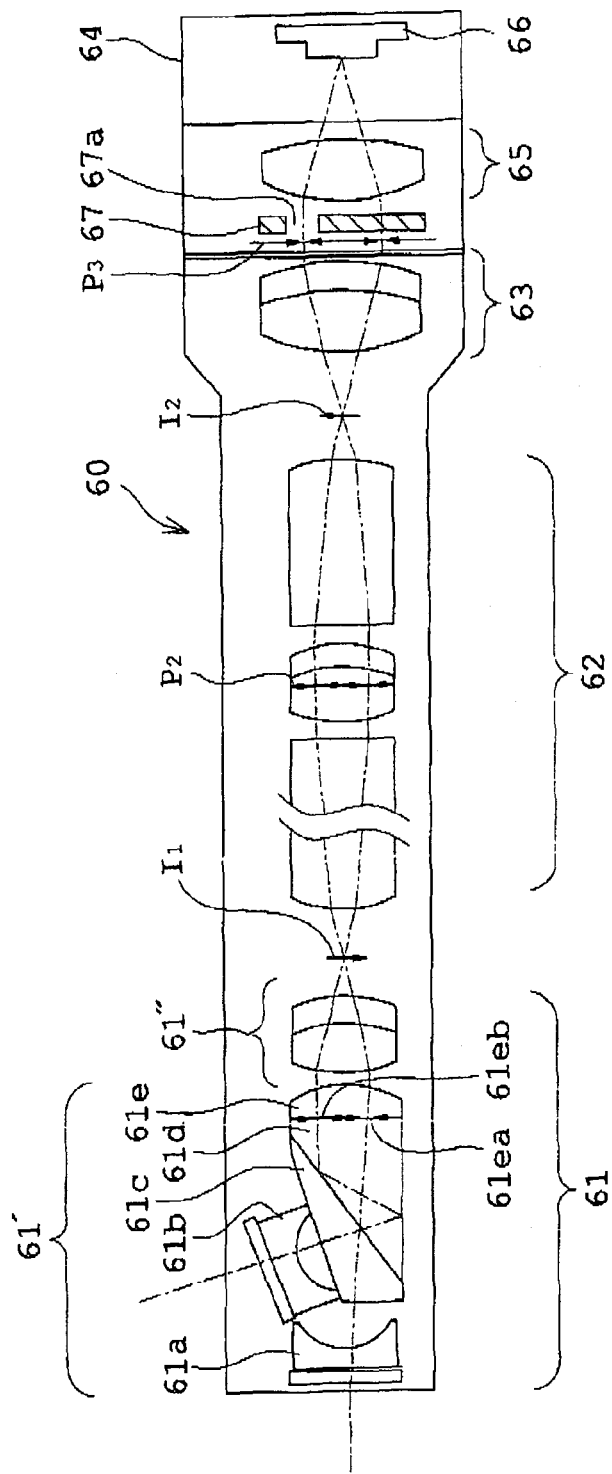
FIGS. 2A and 2B are illustrations showing another conventional example of an optical system which is capable of switching an observation field of view, and show a sectional view along the optical axis and a front view of a pupil-separating stop which is a component of the optical system shown in FIG. 2A, respectively.
Figure 3A:
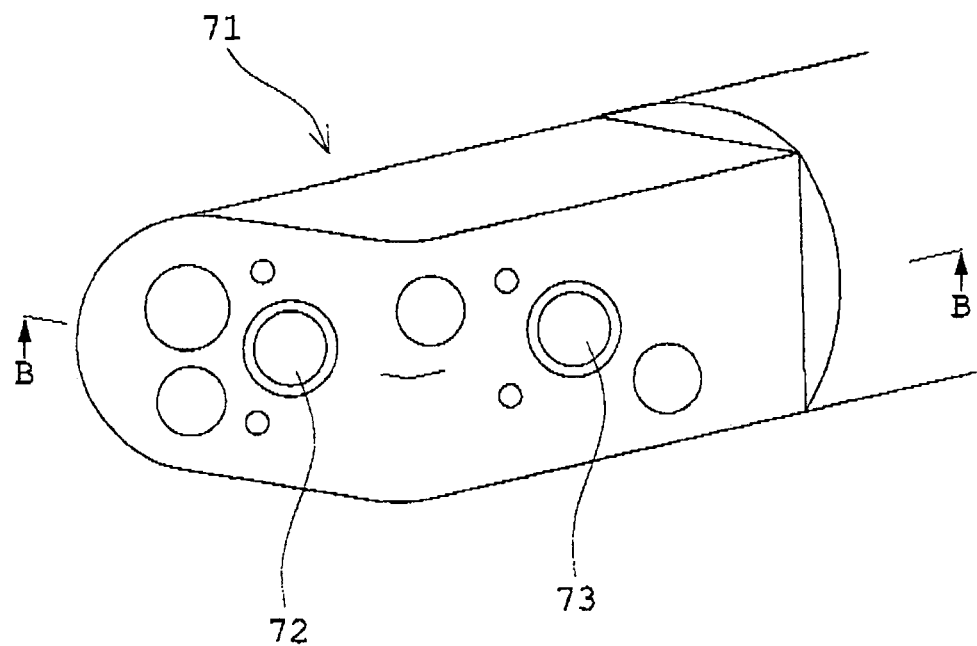
FIGS. 3A and 3B are illustrations showing further another conventional example of an optical system which is capable of switching an observation field of view, and show a schematic view of a tip portion of an endoscope and a B-B sectional view of FIG. 3A, respectively.
Figure 3B:
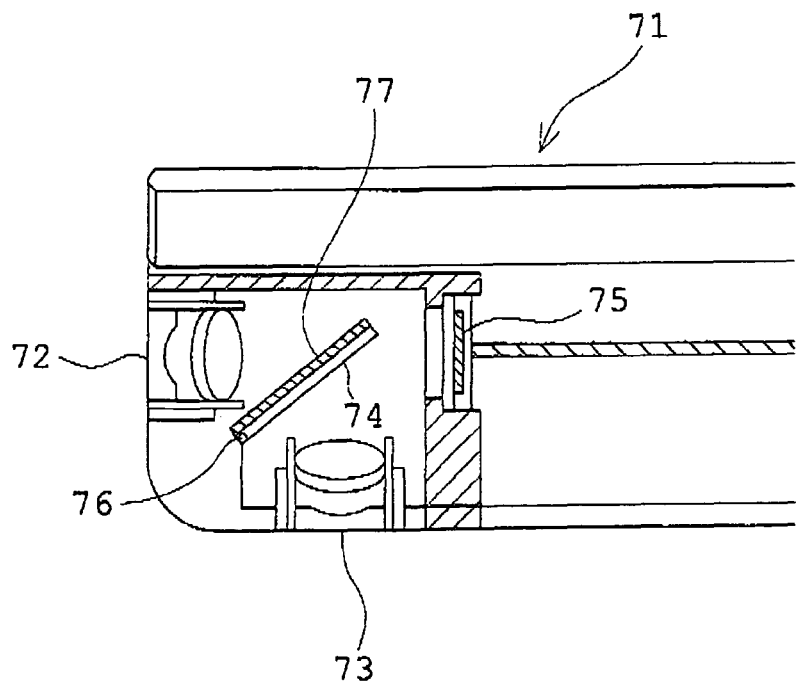
Figure 4:
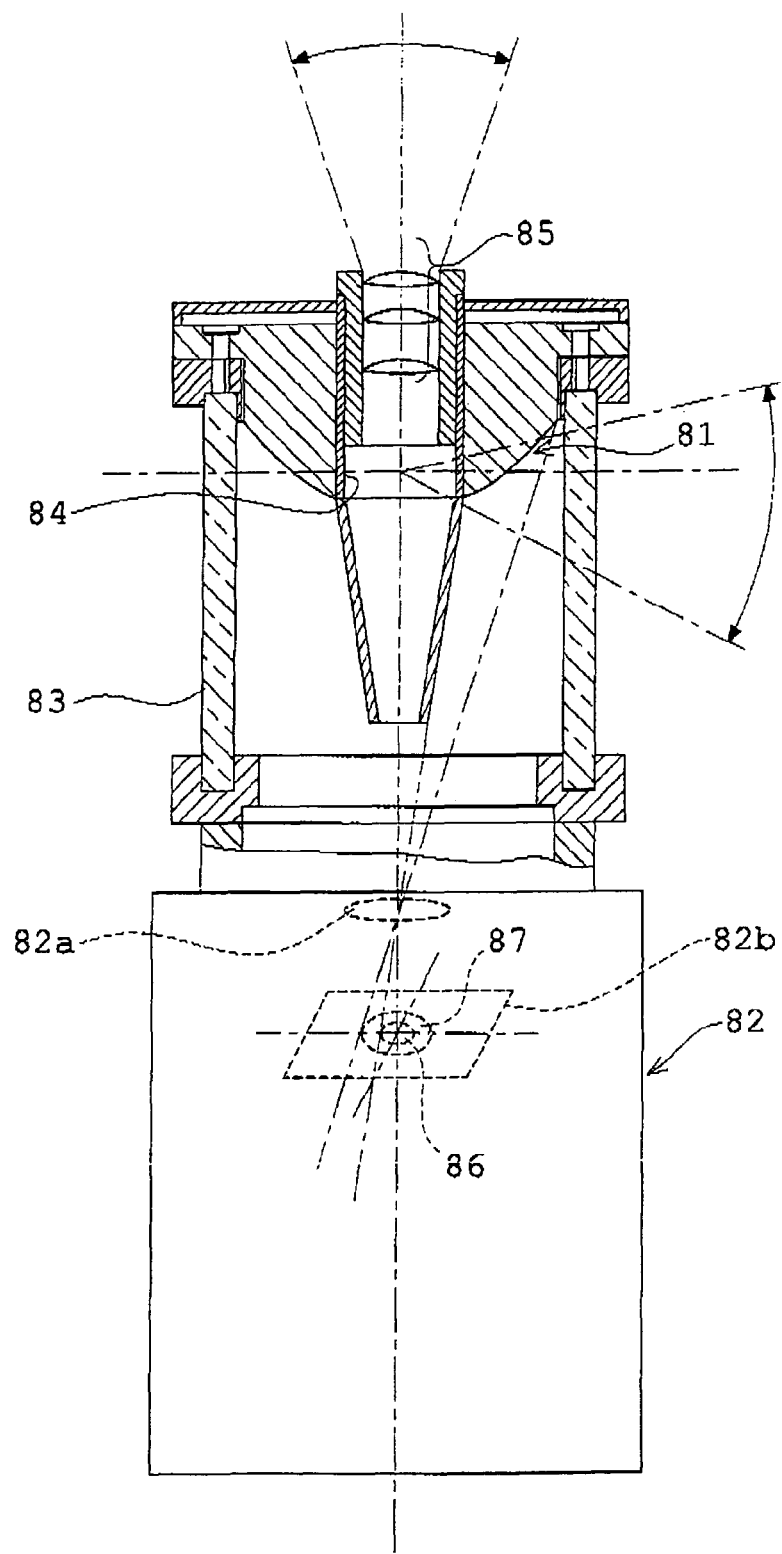
FIG. 4 is an illustration showing one conventional example of an optical system which is capable of performing observations in a forward field of view and in a lateral field of view.
Figure 5:
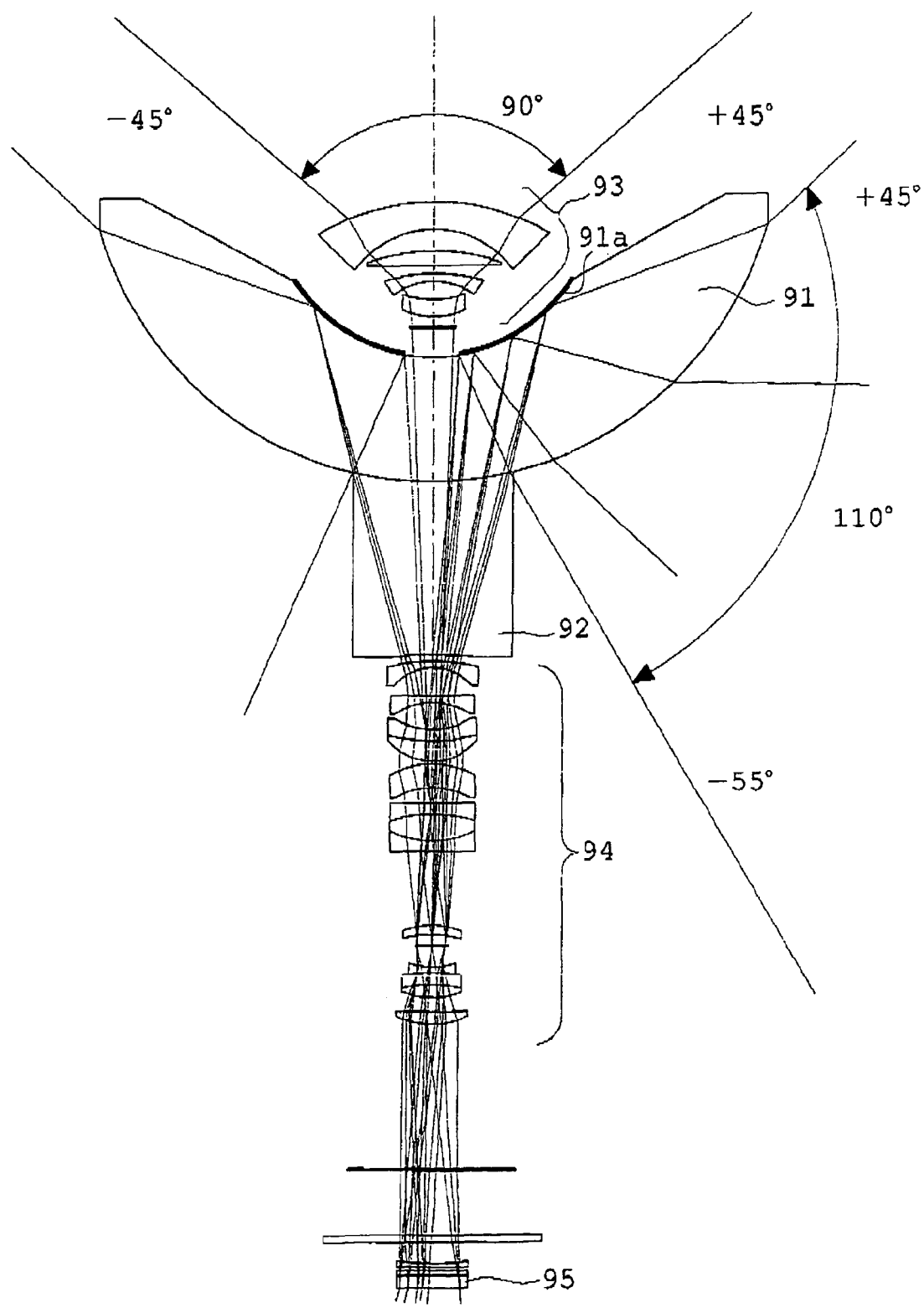
FIG. 5 is an illustration showing another conventional example of an optical system which is capable of performing observations in a forward field of view and in a lateral field of view.
Figure 6:
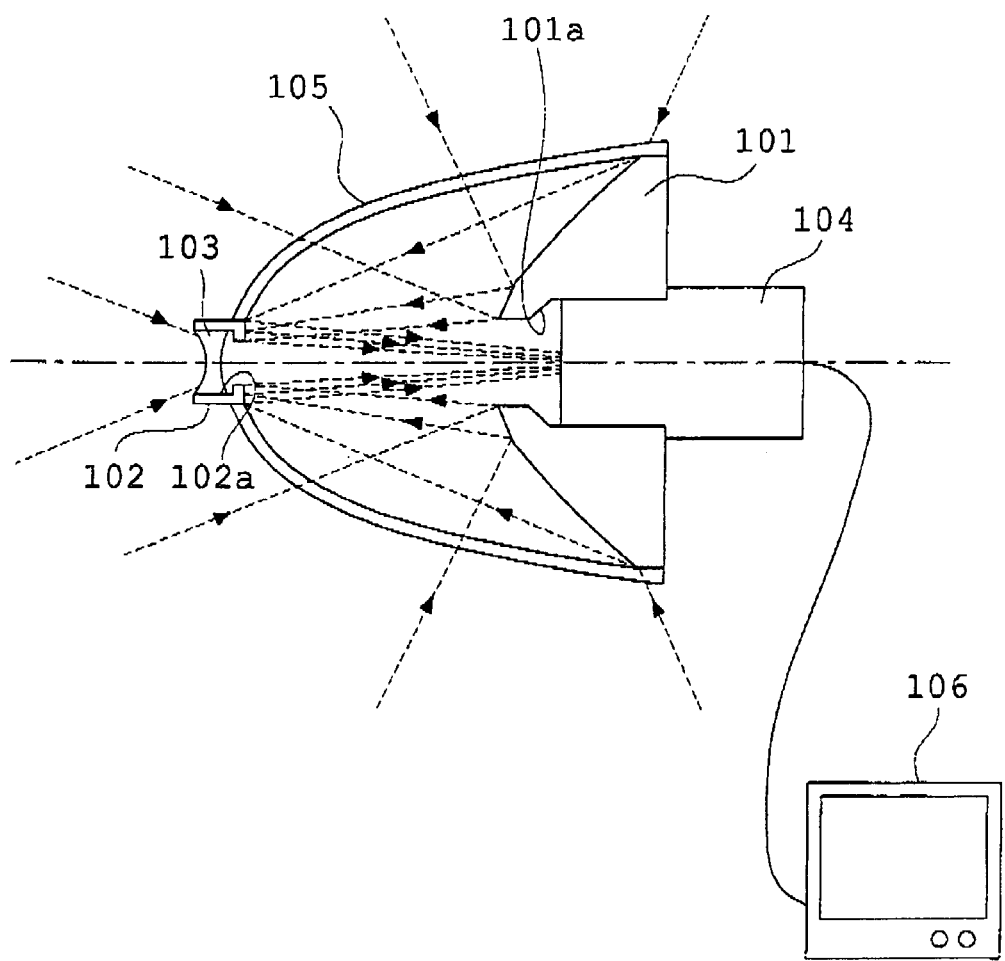
FIG. 6 is an illustration showing further another conventional example of an optical system which is capable of performing observations in a forward field of view and in a lateral field of view.

The entire lateral circumference-observation optical system 2 is an optical system for performing an observation in a field of view of the entire lateral circumference and is composed of an annular prism which is provided with an incidence surface 2b, a transmittance-reflection surface 2c, and a reflection surface 2d while the annular prism is provided with an opening 2a in its central portion. And, the entire lateral circumference-observation optical system 2 functions in such a way that the optical system 2 transmits incident light from the field of view of the entire lateral circumference through the incidence surface 2b, totally reflects the light by the transmittance-reflection surface 2c, reflects the light by the reflection surface 2d, and transmits the light through the transmittance-reflection surface 2c to makes the light go toward the image-forming-optical-system-4 side while the optical system 2 makes light from a forward field of view exiting the forward observation optical system 1 pass through the opening 2a and makes the light go toward the image-forming-optical-system-4 side. Besides, the entire lateral circumference-observation optical system 2 is not limited to the formation shown in FIG. 1.

The variable stop 3 is composed of stops 31 and 32 which are arranged between the entire lateral circumference-observation optical system 2 and the image-forming optical system 4.

The stop 31 is arranged in the vicinity of the entire lateral circumference-observation optical system 2. And, in the opening state, the stop 31 opens: the optical path of light from the forward field of view which exits the forward observation optical system 1 and passes through the opening 2a of the entire lateral circumference-observation optical system 2; and the optical path of light from the field of view of the entire lateral circumference which exits the entire lateral circumference-observation optical system 2. On the other hand, in the closing state, the stop 31 is formed so as to open only the optical path of light from the forward field of view which exits the forward observation optical system 1 and passes through the opening 2a of the entire lateral circumference-observation optical system 2 and so as to close the optical path of light from the field of view of the entire lateral circumference which exits the entire lateral circumference-observation optical system 2.

The stop 32 is arranged on the image side more distantly than the stop 31. And, in the opening state, the stop 32 opens the optical path of light passing through the stop 31. On the other hand, in the closing state, the stop 32 is formed in such a way that, in the light passing through the stop 31, the stop 32 opens: the optical path of light from the forward field of view and in the range N in which the angle of field of view is narrow; and the optical path of light from the field of view of the entire lateral circumference, and the stop 32 intercepts the optical path of light from the forward field of view and in the range W in which the angle of field of view is wide.

Also, the variable stop 3 is formed in such a way that, when one of the stops 31 and 32 is opened, the other stop is stopped down.

And, when an observation field of view is switched to a simultaneous observation in a forward field of view and in the field of view of the entire lateral circumference, the variable stop 3 is in a state in which the stop 31 is opened while the stop 32 is stopped down. In this case, the stop 31 functions as a field stop for the entire lateral circumference-observation optical system 2, and the stop 32 functions as a field stop for light in the range of a wide angle of field of view in the forward observation optical system 1, as an aperture stop for light in the range of a narrow angle of field of view, and as an aperture stop for the lateral periphery-observation optical system 2. On the other hand, when an observation field of view is switched to an observation only in a forward field of view, the variable stop 3 is in a state in which the stop 31 is stopped down while the stop 32 is opened. In this case, the stop 31 functions as an aperture stop for the forward observation optical system 1 and as a field stop for the entire lateral circumference-observation optical system 2, and the stop 32 functions as a field stop for the forward observation optical system 1.

Also, the stops 31 and 32 are composed of aperture blades in common use. Besides, the stops 31 and 32 may be composed of a liquid crystal element.

The image-forming optical system 4 is formed in such a way that the image-forming optical system 4 forms an image on the central region I1 in the image pickup plane of the image pickup element 5 by light from the forward field of view which exits the forward observation optical system 1 and passes through the opening 2a of the entire lateral circumference-observation optical system 2 and the variable stop 3, in such a way that the axes of the chief rays become nearly parallel, while the image-forming optical system 4 forms an image on the surrounding region I2 in the image pickup plane of the image pickup element 5 by light from the entire lateral circumference which exits the entire lateral circumference-observation optical system 2 and passes through the variable stop 3, in such a way that the axes of the chief rays become a nearly parallel.

The operations of the optical system of the first embodiment which is formed in such manner will be explained.

Light from a forward field of view exits the lenses 11 and 12 of the forward observation optical system 1 and passes through the opening 2a of the entire lateral circumference-observation optical system 2. On the other hand, light from a field of view of the entire lateral circumference is transmitted by the incidence surface 2b of the entire lateral circumference-observation optical system 2, is totally reflected by the transmittance-reflection surface 2c, is reflected by the reflection surface 2d, and is transmitted by the transmittance-reflection surface 2c.

Now, when an observation field of view is switched to the simultaneous observation in a forward field of view and in a field of view of the entire lateral circumference, as shown in FIG. 7A, the stop 31 becomes the opening state and the stop 32 becomes the stopped-down state. In this case, both light rays from the forward field of view and light rays from the field of view of the entire lateral circumference, which enter the stop 3, pass through the stop 31. In the light rays passing through the stop 31, light rays from the forward field of view and in the range W in which the angle of field of view is wide are intercepted by the stop 32. On the other hand, after light rays from the forward field of view and in the range N in which the angle of field of view is narrow and light rays from the field of view of the entire lateral circumference pass through the stop 32 while these light rays are crossing one another, the light rays from the forward field of view and in the range N in which the angle of field of view is narrow and the light rays from the field of view of the entire lateral circumference enter the image-forming optical system 4. As shown in FIG. 7B, the light rays from the forward field of view and the light rays from the field of view of the entire lateral circumference, which enter the image-forming optical system 4, form images on the set regions I1 and I2 in the imaging plane 5a of the image pickup element 5 respectively, through the image-forming optical system 4.

On the other hand, when an observation field of view is switched to an observation only in a forward field of view, as shown in FIG. 7C, the stop 31 becomes the stopped-down state and the stop 32 becomes the opening state. In this case, in light rays from the forward field of view and light rays from the field of view of the entire lateral circumference which enter the stop 3, the light rays from the field of view of the entire lateral circumference are intercepted by the stop 31, and only the light rays from the forward field of view pass through the stop 31 while these light rays are crossing one another, pass through the stop 32, and thereafter enter the image-forming optical system 4. As shown in FIG. 7D, the light rays from the forward field of view which enter the image-forming optical system 4 form an image on the whole region I1 of the image pickup plane 5a of the image pickup element 5, through the image-forming optical system 4.

In this case, the variable stop 3 is composed of the stops 31 and 32 in the optical system of the first embodiment, so that it is possible to narrow the angle of field of view of the forward field of view to the utmost by arranging the stop 32 with the stop 32 being as close to the image-forming-optical-system-4 side as possible. As a result, the diameter of the light flux of the light rays from the forward field of view which pass through the stop 32 while the light rays are crossing one another becomes small to the utmost, and the region I1 on the image pickup plane of the image pickup element 5 on which an image is formed through the image-forming optical system 4 becomes small to the utmost. As a result, it is possible to make a relatively wide image-forming region I2 on the image pickup plane for an observation image from the field of view of the entire lateral circumference.

On the other hand, the stop 31 is arranged at the position at which the stop 31 is nearer to the forward observation optical system 1 than the stop 32, so that it is possible to make the angle of field of view of the forward field of view as wide as possible by arranging the stop 31 with the stop 31 being as close to the entire lateral circumference-observation-optical-system-2 side as possible. As a result, the diameter of the light flux of the light rays from the forward field of view which pass through the stop 31 while the light rays are crossing one another becomes large to the utmost, and it is possible to make the region I1 as large as possible, where the region I1 is a region on the image pickup plane of the image pickup element 5 on which an image is formed through the image-forming optical system 4.

So, according to the optical system of the first embodiment, it is possible to switch to an observation only in a forward field of view and to a simultaneous observation in a forward field of view and in a field of view of the entire lateral circumference. And, in the observation state in a simultaneous observation in a forward field of view and in a field of view of the entire lateral circumference, it is possible to make the image-forming region for an observation image from the field of view of the entire lateral circumference as large as possible, and it is possible to observe an observation image of the field of view of the entire lateral circumference in detail. Also, in the observation state in an observation only in a forward field of view, it is possible to make the image-forming region for an observation image from the forward field of view as large as possible, and it is possible to observe an observation image in the forward field of view in detail.

Besides, the entire lateral circumference-observation optical system is composed of the annular prism 2 in the example of FIG. 7. However, as another example, for example, as shown in FIG. 8, the entire lateral circumference-observation optical system may be composed of an annular mirror 2' which is provided with a convex-shaped reflexive surface 2a' which reflects light from the field of view of the entire lateral circumference toward the image-forming-optical-system-4 side.

Also, the optical system of the example shown in FIG. 7 is formed as an image-side telecentric optical system. However, as shown in FIG. 8, the optical system may be formed as an optical system which is not telecentric.

Embodiment 2

Figure 9A:
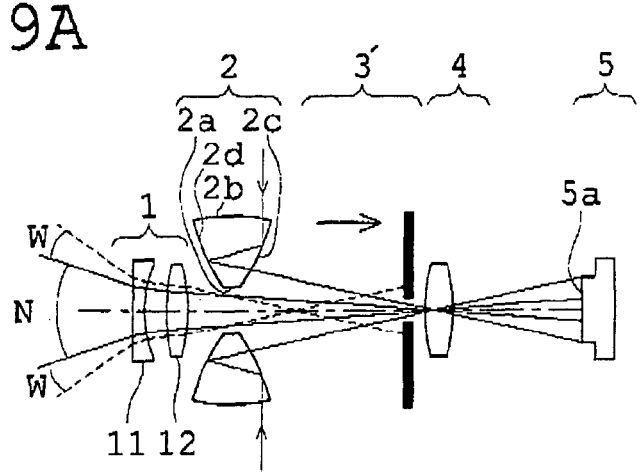
FIGS. 9A, 9B, 9C, and 9D are illustrations showing the schematic formation of an optical system according to the second embodiment of the present invention, and show: a sectional view taken along the optical axis and showing an observation state in a simultaneous observation in a forward field of view and in a field of view of the entire lateral circumference; an illustration showing an image-forming region for an observation image in each of the forward field of view and the field of view of the entire lateral circumference in the imaging plane of an image pickup element in the observation state shown in FIG. 9A; a sectional view taken along the optical axis and showing an observation state in an observation only in a forward field of view; and an illustration showing an image-forming region for an observation image in the forward field of view in the imaging plane of the image pickup element in the observation state shown in FIG. 9C, respectively.
Figure 9B:
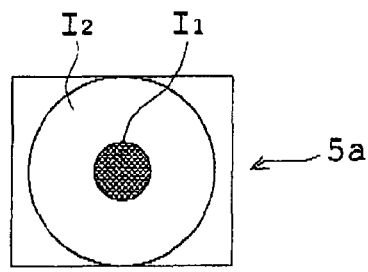
Figure 9C:
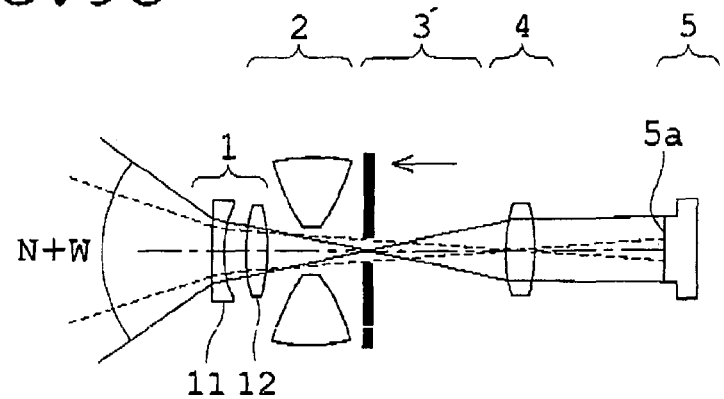
Figure 9D:
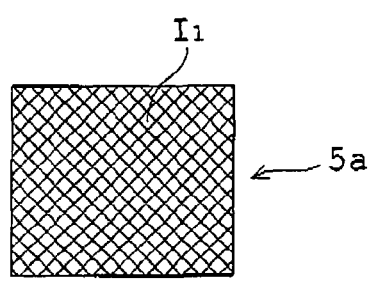
Figure 10A:
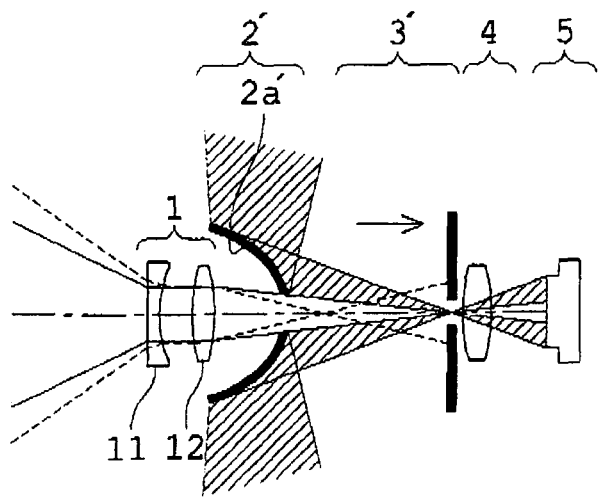
FIGS. 10A and 10B are illustrations showing one example of variations of the optical system shown in FIG. 9, and show: a sectional view taken along the optical axis and showing an observation state in a simultaneous observation in a forward field of view and in a field of view of the entire lateral circumference; and a sectional view taken along the optical axis and showing an observation state in a observation only in a forward field of view, respectively.
Figure 10B:
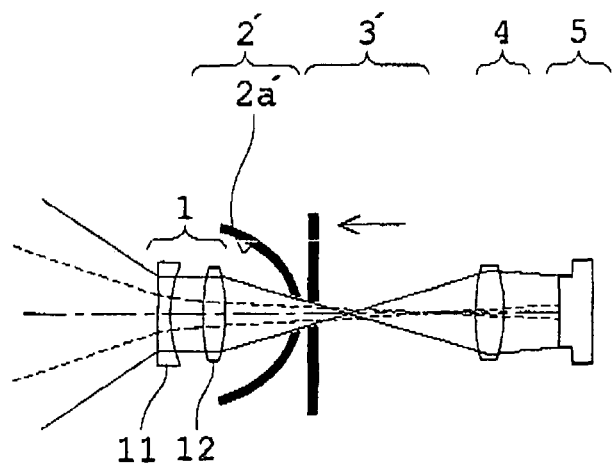

FIGS. 9A, 9B, 9C, and 9D are illustrations showing the schematic formation of an optical system according to the second embodiment of the present invention, and FIG. 9A is a sectional view taken along the optical axis and showing an observation state in a simultaneous observation in a forward field of view and in a field of view of the entire lateral circumference, FIG. 9B is an illustration showing an image-forming region for an observation image in each of the forward field of view and the field of view of the entire lateral circumference in the image pickup plane of an image pickup element in the observation state shown in FIG. 9A, FIG. 9C is a sectional view taken along the optical axis and showing an observation state in an observation only in a forward field of view, and FIG. 9D is an illustration showing an image-forming region for an observation image in the forward field of view in the image pickup plane of the image pickup element in the observation state shown in FIG. 9C. FIGS. 10A and 10B are illustrations showing one example of variations of the optical system shown in FIG. 9, and FIG. 10A is a sectional view taken along the optical axis and showing an observation state in a simultaneous observation in a forward field of view and in a field of view of the entire lateral circumference, and FIG. 10B is a sectional view taken along the optical axis and showing an observation state in a observation only in a forward field of view. Besides, components for the present embodiment which are nearly the same as those of the first embodiment are given the same reference numeral as those of the first embodiment, and the detailed explanations of the components are omitted.

An optical system of the second embodiment is formed in such a way that a variable stop 3' moves on the optical axis between an entire lateral circumference-observation optical system 2 and an image-forming optical system 4.

In the detailed explanation, the diameter of the variable stop 3' is stopped down at set size. And, as shown in FIG. 9A, when the variable stop 3' becomes closest to the image-forming optical system 4, the variable stop 3' opens: the optical path of light from the forward field of view and in the range in which the angle of field of view is narrow, which exits the forward observation optical system 1 to pass through an opening 2a of the entire lateral circumference-observation optical system 2; and the optical path of light from the field of view of the entire lateral circumference which exits the entire lateral circumference-observation optical system 2, and the variable stop 3' intercepts the optical path of light from the forward field of view and in the range in which the angle of field of view is wide, which exits the forward observation optical system 1. On the other hand, as shown in FIG. 9C, the variable stop 3' is formed in such a way that, when variable stop 3' becomes closest to the entire lateral circumference-observation optical system 2, the variable stop 3' opens only the optical path of light from the forward field of view which exits the forward observation optical system 1 to pass through an opening 2a of the entire lateral circumference-observation optical system 2, and the variable stop 3' intercepts the optical path of the light from the field of view of the entire lateral circumference which exits the entire lateral circumference-observation optical system 2.

And, when an observation field of view is switched to a simultaneous observation in a forward field of view and in a field of view of the entire lateral circumference, the variable stop 3' becomes the state in which the stop 3' is closest to the image-forming optical system 4. In this case, the variable stop 3' functions as a field stop for light in the range of the wide angle of field of view in the forward observation optical system 1, as an aperture stop for light in the range of the narrow angle of field of view, and as an aperture stop for the entire lateral circumference-observation optical system 2. On the other hand, when an observation field of view is switched to an observation only in a forward field of view, the variable stop 3' becomes the state which the stop 3' is closest to the entire lateral circumference-observation optical system 2. In this case, the variable stop 3' functions as an aperture stop for the forward observation optical system 1 and as a field stop for the entire lateral circumference-observation optical system 2.

Also, the variable stop 3' is composed of aperture blades in common use. Besides, the variable stop 3' may be composed of a liquid crystal element.

Also, the optical system of the example shown in FIG. 9 is formed as an optical system which is not telecentric. However, the optical system may be formed as an image-side telecentric optical system.

The other constitutions are nearly the same as those of the optical system of the first embodiment.

The operations of the optical system of the second embodiment which is formed in such manner will be explained.

Light from a forward field of view exits lenses 11 and 12 of the forward observation optical system 1 and passes through the opening 2a of the entire lateral circumference-observation optical system 2. On the other hand, Light from a field of view of the entire lateral circumference is transmitted by an incidence surface 2b of the entire lateral circumference-observation optical system 2, is totally reflected by a transmittance-reflection surface 2c, is reflected by a reflection surface 2d, and is transmitted by the transmittance-reflection surface 2c.

Now, when an observation field of view is switched to the simultaneous observation in a forward field of view and in a field of view of the entire lateral circumference, as shown in FIG. 9A, the variable stop 3' becomes the state in which the stop 3' is closest to the image-forming optical system 4. In this case, in the light rays from the forward field of view and light rays from the field of view of the entire lateral circumference which enter the variable stop 3', light rays from the forward field of view and in the range W in which the angle of field of view is wide are intercepted by the variable stop 3'. On the other hand, after light rays from the forward field of view and in the range N in which the angle of field of view is narrow and light rays from the field of view of the entire lateral circumference pass through the variable stop 3' while these light rays are crossing one another, the light rays from the forward field of view and in the range N in which the angle of field of view is narrow and the light rays from the field of view of the entire lateral circumference enter the image-forming optical system 4. As shown in FIG. 9B, the light rays from the forward field of view and the light rays from the field of view of the entire lateral circumference, which enter the image-forming optical system 4, form images on the set regions I1 and I2 in the image pickup plane 5a of the image pickup element 5 respectively, through the image-forming optical system 4.

On the other hand, when an observation field of view is switched to the observation only in a forward field of view, as shown in FIG. 9C, the variable stop 3' becomes the state in which the stop 3' is closest to the entire lateral circumference-observation optical system 2. In this case, in the light rays from forward field of view and light rays from the field of view of the entire lateral circumference which enter the variable stop 3', the light rays from the field of view of the entire lateral circumference are intercepted by the variable stop 3', and only the light rays from the forward field of view pass through the variable stop 3' and thereafter enter the image-forming optical system 4. As shown in FIG. 9D, the light rays from the forward field of view which enter the image-forming optical system 4 form an image on the whole region I1 of the image pickup plane 5a of the image pickup element 5, through the image-forming optical system 4.

In this case, in the optical system of the second embodiment, the variable stop 3' is formed so as to move on the optical axis between the entire lateral circumference-observation optical system 2 and the image-forming optical system 4, so that it is possible to narrow the angle of field of view of the forward field of view to the utmost by making the variable stop 3' as close to the image-forming-optical-system-4 side as possible. As a result, the diameter of the light flux of the light rays from the forward field of view which pass through the variable stop 3' while the light rays are crossing one another becomes small to the utmost, and the region I1 on the image pickup plane of the image pickup element 5 on which an image is formed through the image-forming optical system 4 becomes small to the utmost. As a result, it is possible to make a relatively wide image-forming region I2 on the image pickup plane for an observation image from the field of view of the entire lateral circumference to the utmost.

On the other hand, it is possible to make the angle of field of view of the forward field of view as wide as possible by making the variable stop 3' as close to the entire lateral circumference observation optical system 2 as possible. As a result, the diameter of the light flux of the light rays from the forward field of view which pass through the variable stop 3' while the light rays are crossing one another becomes large to the utmost, and it is possible to make the region I1 as large as possible, where the region I1 is a region on the image pickup plane of the image pickup element 5 on which an image is formed through the image-forming optical system 4.

So, according to the optical system of the second embodiment, it is possible to switch to an observation only in a forward field of view and to a simultaneous observation in a forward field of view and in a field of view of the entire lateral circumference. And, in the observation state in a simultaneous observation in a forward field of view and in a field of view of the entire lateral circumference, it is possible to make the image-forming region for an observation image from the field of view of the entire lateral circumference as large as possible, and it is possible to observe an observation image in the field of view of the entire lateral circumference in detail. Also, in the observation state in an observation only in a forward field of view, it is possible to make the image-forming region for an observation image from the forward field of view as large as possible, and it is possible to observe an observation image in the forward field of view in detail.

Also, in the optical system of the second embodiment, the variable stop 3' is formed so as to move on the optical axis between the entire lateral circumference-observation optical system 2 and the image-forming optical system 4, so that the ratio of the size of the image-forming region for an observation image from the forward field of view to the size of the image-forming region for an observation image from the field of view of the entire lateral circumference continuously varies in accordance with position of the variable stop 3'. So, according to the optical system of the second embodiment, it is possible to adjust the ratio of the size of the image-forming region for an observation image from the forward field of view to the size of the image-forming region for an observation image from the field of view of the entire lateral circumference to change the ratio into a desired ratio, in accordance with use for observation.

Also, according to the optical system of the second embodiment, it is possible to make a variable stop of a single component, and it is possible to decrease the number of the total of the components the more.

Besides, the entire lateral circumference-observation optical system is composed of the annular prism 2 in the example of FIG. 9. However, as another example, for example, as shown in FIG. 10, the entire lateral circumference-observation optical system may be composed of an annular mirror 2' which is provided with a convex-shaped reflexive surface 2a' which reflects light from the field of view of the entire lateral circumference toward the image-forming-optical-system-4 side.

Embodiment 3

Figure 11A:
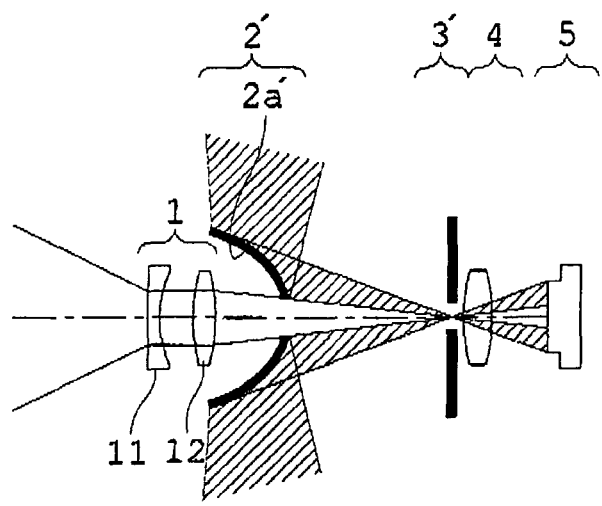
FIGS. 11A and 11B are illustrations showing the schematic formation of an optical system according to the third embodiment of the present invention, and show: a sectional view taken along the optical axis and showing an observation state in a simultaneous observation in a forward field of view and in a field of view of the entire lateral circumference; and a sectional view taken along the optical axis and showing an observation state in an observation only in a forward field of view, respectively.
Figure 11B:
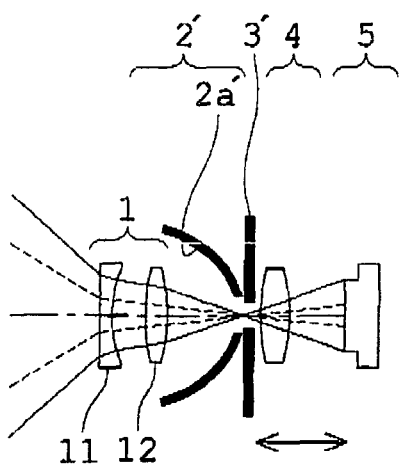

FIGS. 11A and 11B are illustrations showing the schematic formation of an optical system according to the third embodiment of the present invention, and FIG. 11A is a sectional view taken along the optical axis and showing an observation state in a simultaneous observation in a forward field of view and in a field of view of the entire lateral circumference, and FIG. 11B is a sectional view taken along the optical axis and showing an observation state in an observation only in a forward field of view.

The optical system of the third embodiment is formed in such a way that an image-forming optical system 4 and an image pickup element 5 move integratedly with a variable stop 3' in the formation of the second embodiment which is shown as an example of variations in FIG. 10.

The other constitutions are nearly the same as those of the optical system of the second embodiment.

In the formations for the second embodiment shown in FIGS. 9 and 10, when observations in a forward field of view and in a field of view of the entire lateral circumference are performed simultaneously, it is desirable to make the variable stop 3' as close to the image-forming optical system 4 as possible in order to make the ratio of the image-forming region for an observation image in the forward field of view as small as possible. On the other hand, when an observation only in a forward field of view is performed, it is desirable to make the variable stop 3' as close to the entire lateral circumference-observation optical system 2 (2') as possible in order to observe an observation image in a wide-angle field of view.

When the variable stop 3' is made to get closest to the entire lateral circumference-observation optical system 2 (2'), the distance between the variable stop 3' and the image-forming optical system 4 becomes farthest away.

Now, as the distance between the variable stop 3' and the image-forming optical system 4 becomes farther away, light rays which are transmitted by the variable stop 3' while the light rays are crossing one another and which go toward the image-forming optical system 4 spread more.

Accordingly, in the formations shown in FIGS. 9 and 10, the image-forming optical system 4 is liable to become large when all of light rays exiting the forward observation optical system 1 are made to enter the image-forming optical system 4 in an observation only in a forward field of view.

Whereas, according to the optical system of the third embodiment, the image-forming optical system 4 and the image pickup element 5 move integratedly with the variable stop 3', so that it is possible to keep the relative positional relation between the variable stop 3', the image-forming optical system 4, and the image pickup element 5 constant, and it is possible to avoid the image-forming optical system 4 having a large size. So, according to the optical system of the third embodiment, when the optical system of the third embodiment is used for an endoscope for observing the inside of a tubule in a living body, or the like, it is possible to make a small diameter of the tip of an endoscope or the like, and a large effect on a reduction of a burden on the human body is acquired.

The other operation effects are nearly the same as those of the optical system of the second embodiment.

Embodiment 4

Figure 12A:
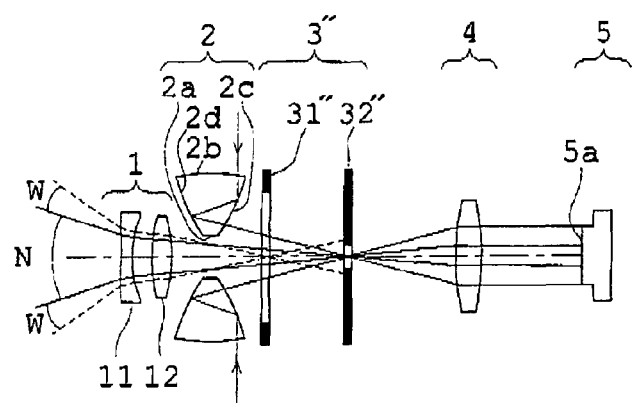
FIGS. 12A, 12B, 12C, 12D, 12E and 12F are illustrations showing the schematic formation of an optical system according to the fourth embodiment of the present invention, and show: a sectional view taken along the optical axis and showing an observation state in a simultaneous observation in a forward field of view and in a field of view of the entire lateral circumference; an illustration showing an image-forming region for an observation image in each of the forward field of view and the field of view of the entire lateral circumference in the image pickup plane of an image pickup element in the observation state shown in FIG. 12A; a sectional view taken along the optical axis and showing an observation state in an observation only in a forward field of view; an illustration showing an image-forming region for an observation image in the forward field of view in the image pickup plane of the image pickup element in the observation state shown in FIG. 12C; a sectional view taken along the optical axis and showing an observation state in an observation only in a field of view of the entire lateral circumference; and an illustration showing an image-forming region for an observation image in the field of view of the entire lateral circumference in the image pickup plane of the image pickup element in the observation state shown in FIG. 12E, respectively.
Figure 12B:
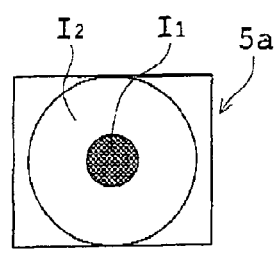
Figure 12C:
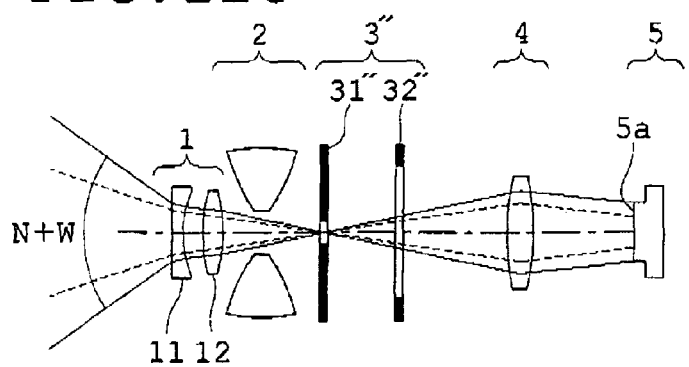
Figure 12D:
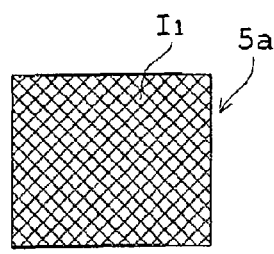
Figure 12E:
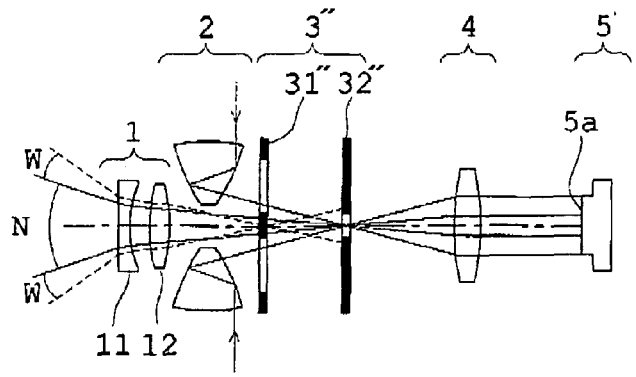
Figure 12F:
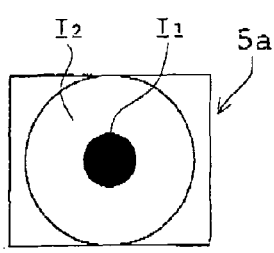

FIGS. 12A, 12B, 12C, 12D, 12E and 12F are illustrations showing the schematic formation of an optical system according to the fourth embodiment of the present invention, and FIG. 12A is a sectional view taken along the optical axis and showing an observation state in a simultaneous observation in a forward field of view and in a field of view of the entire lateral circumference, FIG. 12B is an illustration showing an image-forming region for an observation image in each of the forward field of view and the field of view of the entire lateral circumference in the image pickup plane of an image pickup element in the observation state shown in FIG. 12A, FIG. 12C is a sectional view taken along the optical axis and showing an observation state in an observation only in a forward field of view, FIG. 12D is an illustration showing an image-forming region for an observation image in the forward field of view in the image pickup plane of the image pickup element in the observation state shown in FIG. 12C, FIG. 12E is a sectional view taken along the optical axis and showing an observation state in an observation only in a field of view of the entire lateral circumference, and FIG. 12F is an illustration showing an image-forming region for an observation image in the field of view of the entire lateral circumference in the image pickup plane of the image pickup element in the observation state shown in FIG. 12E.

In the optical system of the fourth embodiment, a variable stop 3" which is composed of liquid crystal elements 31" and 32" is arranged between an entire lateral circumference-observation optical system 2 and an image-forming optical system 4 instead of the variable stop 3 for the optical system of the first embodiment shown in FIG. 7.

The liquid crystal element 31" is arranged in the vicinity of the entire lateral circumference-observation optical system 2. The liquid crystal element 32" is arranged on the image side more distantly than the liquid crystal element 31".

And, the variable stop 3" is formed in such a way that the states of the liquid crystal elements 31" and 32" stopping down vary in accordance with a switch to the following three observation fields of view.

When an observation field of view is switched to the observation field of view for an observation only in a forward field of view as the first observation field of view, as shown in FIG. 12C, the liquid crystal element 31" opens only the optical path of light from the forward field of view which exits a forward observation optical system 1 and passes through an opening 2a of an entire lateral circumference-observation optical system 2, and the liquid crystal element 31" intercepts the optical path of light from a field of view of the entire lateral circumference which exits the entire lateral circumference-observation optical system 2, while the liquid crystal element 32" opens the optical path of the light which is transmitted by the liquid crystal element 31".

When an observation field of view is switched to the observation field of view for a simultaneous observation in a forward field of view and in a field of view of the entire lateral circumference as the second observation field of view, as shown in FIG. 12A, the liquid crystal element 31" opens: the optical path of light from the forward field of view which exits a forward observation optical system 1 and passes through the opening 2a of the entire lateral circumference-observation optical system 2; and the optical path of light from the field of view of the entire lateral circumference which exits the entire lateral circumference-observation optical system 2. And, in the light transmitted by the liquid crystal element 31", the liquid crystal element 32" opens: the optical path of light from the forward field of view and in the range N in which the angle of field of view is narrow; and the optical path of the light from the field of view of the entire lateral circumference, and the liquid crystal element 32" intercepts the optical path of light from the forward field of view and in the range W in which the angle of field of view is wide.

When an observation field of view is switched to the observation field of view for an observation only in a field of view of the entire lateral circumference as the third observation field of view, as shown in FIG. 12E, the liquid crystal element 31" intercepts the optical path of light from the forward field of view which exits a forward observation optical system 1 and passes through the opening 2a of the entire lateral circumference-observation optical system 2, and the liquid crystal element 31" opens only the optical path of light from the field of view of the entire lateral circumference which exits the entire lateral circumference-observation optical system 2, while the liquid crystal element 32" stops down the optical paths of the light transmitted by the liquid crystal element 31".

The other constructions are nearly the same as those of the optical system of the first embodiment.

In the optical system of the fourth embodiment having such formation, the image-forming regions for observation images from a forward field of view and from a field of view of the entire lateral circumference produce the same effects as those of the optical system of the first embodiment as shown in FIGS. 12D and 12B respectively, in observations in the first observation field of view (the observation field of view for an observation only in a forward field of view) and in an observation in the second observation field of view (the observation field of view for a simultaneous observation in a forward field of view and in a field of view of the entire lateral circumference).

In addition, in the optical system of the fourth embodiment, when an observation is performed in the third observation field of view (the observation field of view for an observation only in a field of view of the entire lateral circumference), light from a forward field of view is intercepted by the liquid crystal element 31" and only light from the field of view of the entire lateral circumference is transmitted by the liquid crystal element 31", in light incident on the variable stop 3". The light rays transmitted by the liquid crystal element 31" are transmitted by the liquid crystal element 32" while the light rays are being crossing one another, and thereafter enter the image-forming optical system 4. The light rays from the field of view of the entire lateral circumference which enter the image-forming optical system 4 form an image on a set region I2 on the image pickup plane 5a of the image pickup element 5 through the image-forming optical system 4, as shown in FIG. 12F. And, a set region I1 on the image pickup plane of the image pickup element 5 becomes dark.

In an observation of the inside of a pipe, when the distance between an observed object in a forward field of view and an observation optical system is close, the intensity of reflection light to illumination light which comes from the observed object located in the forward field of view and is incident on the observation optical system may become too high. In such a case, when a simultaneous observation in a forward field of view and in a field of view of the entire lateral circumference is performed, for example, an observation image from the field of view of the entire lateral circumference becomes relatively dark because an observation image from the forward field of view is too bright. As a result, it is difficult to perform an observation.

Whereas, according to the optical system of the fourth embodiment, the variable stop 3" is composed of the liquid crystal elements 31" and 32" which open optical paths, in order to deal with a switch to an observation in the observation field of view for an observation only in a field of view of the entire lateral circumference as the third observation field of view together with observations in the first observation field of view (the observation field of view for an observation only in a forward field of view) and in the second observation field of view (the observation field of view for a simultaneous observation in a forward field of view and in a field of view of the entire lateral circumference) which are the same as those of the optical system of the first embodiment respectively, so that, by switching to an observation in the third observation field of view after an observed position in the direction of insertion is identified by a simultaneous observation in the forward field of view at the narrow angle and in the field of view of the entire lateral circumference in an observation in the second observation field of view, it is possible to observe an observation image from the field of view of the entire lateral circumference with good brightness in detail.

The present invention is useful for fields of medicine and industry which demand a diagnosis by an observation of the inside of a pipe using an endoscope or the like.

What is claimed is:

1. An optical system that forms a path of image forming light from an object, comprising, in order from an object side to an image side along a single optical axis:
   a front observation optical system;
   a full-circumference lateral observation optical system substantially having a rotationally symmetric shape about the optical axis;
   a variable stop; and
   an image-forming optical system,
   wherein the variable stop includes, in order from the object side to the image side, a first stop and a second stop serially arranged in the path of image forming light from the object, and
   wherein each of the first stop and the second stop is configured to be switchable between an opened state and a stopped-down state so that:
      the first stop, in the opened state, transmits light from the front observation optical system and light from the full-circumference lateral observation optical system and, in the stopped-down state, transmits only light from the front observation optical system and intercepts light from the full-circumference lateral observation optical system, and
      the second stop, in the opened state, transmits light having been transmitted through the first stop, and, in the stopped-down state, transmits light from the full-circumference lateral observation optical system and, out of light from the front observation optical system, light with an angle of view narrower than the light transmitted through the opened-state first stop.

2. The optical system according to claim 1, wherein the variable stop is configured to be switchable between:
 a first state where the first stop is in the opened state and the second stop is in the stopped-down state; and
 a second state where the first stop is in the stopped-down state and the second stop is in the opened state.

\* \* \* \* \*